United States Patent
Boutte et al.

(10) Patent No.: US 9,498,169 B1
(45) Date of Patent: *Nov. 22, 2016

(54) IMAGING SHEET AND RELATED METHOD

(71) Applicant: BEEKLEY CORPORATION, Bristol, CT (US)

(72) Inventors: Martine M Boutte, South Glastonbury, CT (US); Raymond Thomas, Douglassville, PA (US)

(73) Assignee: Beekley Corporation, Bristol, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/271,370

(22) Filed: May 6, 2014

Related U.S. Application Data

(63) Continuation of application No. 13/846,114, filed on Mar. 18, 2013, now Pat. No. 8,718,229, which is a continuation of application No. 12/604,049, filed on Oct. 22, 2009, now Pat. No. 8,401,145.

(60) Provisional application No. 61/107,967, filed on Oct. 23, 2008.

(51) Int. Cl.
*A61B 6/04* (2006.01)
*A61B 6/00* (2006.01)

(52) U.S. Cl.
CPC ............... *A61B 6/04* (2013.01); *A61B 6/4423* (2013.01); *A61B 6/502* (2013.01)

(58) Field of Classification Search
CPC ...... A61B 6/502; A61B 6/0412; A61B 6/06; A61B 6/4233; A61B 6/0431; A61B 2562/14; A61B 6/0407; A61B 6/04; A61B 6/4423; C08L 33/14; C08L 2666/02; A61L 24/043; A61L 31/041; A61L 17/10; A61L 2400/04; C04B 14/28; C04B 28/14; C04B 22/064; C04B 24/26; C04B 14/26; C04B 14/30; C04B 14/303; C04B 14/305; C04B 14/36; C04B 14/386
USPC ............................ 378/37, 206, 208, 189, 177
See application file for complete search history.

(56) References Cited

U.S. PATENT DOCUMENTS

| | | |
|---|---|---|
| 3,332,646 A | 7/1967 | Kellett |
| 3,578,971 A | 5/1971 | Lasky |

(Continued)

FOREIGN PATENT DOCUMENTS

| | | |
|---|---|---|
| DE | 199 26 446 A1 | 1/2000 |
| DE | 199 21 100 A1 | 3/2000 |

(Continued)

OTHER PUBLICATIONS

I. Krucinska et al., Modified Rheological Model for Analysis of Compression on Nonwoven Fabrics, Textile Research Journal, vol. 74(2), 127-133 (2004).

(Continued)

*Primary Examiner* — Glen Kao
(74) *Attorney, Agent, or Firm* — McCarter & English, LLP

(57) ABSTRACT

A flexible, durable, sanitary, adhesive-backed sheet is applied to the skin-contacting surfaces of a mammography bucky prior to commencing a mammography procedure, and is removed from the bucky once the procedure is complete, without leaving a residue behind. The sheet is made of a non-woven polymeric material that gives the sheet a fabric-like or cloth feel, and is substantially incompressible in response to forces applied during a mammography procedure. The sheet insulates the patient from the temperature differential between the patient's skin and the bucky surfaces. Additionally, the surface of the sheet is embossed with a texture, markings or raised features to enhance the fabric-like feel.

30 Claims, 4 Drawing Sheets

(56) References Cited

U.S. PATENT DOCUMENTS

| | | | |
|---|---|---|---|
| 5,044,008 A | 8/1991 | Jackson | |
| 5,081,657 A | 1/1992 | Klawitter et al. | |
| 5,115,544 A | 5/1992 | Widen | |
| 5,185,776 A | 2/1993 | Townsend | |
| 5,226,070 A | 7/1993 | Ariba et al. | |
| 5,311,883 A | 5/1994 | Sherman | |
| 5,377,254 A | 12/1994 | Walling | |
| 5,386,447 A * | 1/1995 | Siczek | A61B 6/502 378/37 |
| 5,398,272 A | 3/1995 | Bouscary et al. | |
| 5,399,174 A | 3/1995 | Yeo et al. | |
| 5,479,927 A | 1/1996 | Shmulewitz | |
| 5,541,972 A | 7/1996 | Anthony | |
| 5,719,916 A | 2/1998 | Nelson et al. | |
| 6,049,583 A | 4/2000 | Galkin | |
| 6,577,702 B1 | 6/2003 | Lebovic et al. | |
| 6,765,984 B2 | 7/2004 | Higgins et al. | |
| 6,850,590 B2 | 2/2005 | Galkin | |
| 6,968,033 B2 | 11/2005 | Lebovic et al. | |
| 6,975,701 B2 | 12/2005 | Galkin | |
| 7,251,309 B2 | 7/2007 | Galkin | |
| 7,502,441 B2 | 3/2009 | Lebovic et al. | |
| 8,401,145 B1 * | 3/2013 | Boutte | A61B 6/502 378/37 |
| 8,718,229 B1 * | 5/2014 | Boutte et al. | 378/37 |
| 2003/0007597 A1 | 1/2003 | Higgins et al. | |
| 2003/0121899 A1 | 7/2003 | Argersinger et al. | |
| 2004/0082929 A1 | 4/2004 | Arora et al. | |
| 2004/0149711 A1 | 8/2004 | Wyatt et al. | |
| 2004/0206738 A1 | 10/2004 | Argersinger et al. | |
| 2004/0218727 A1 | 11/2004 | Shoenfeld | |
| 2005/0036584 A1 | 2/2005 | Lebovic et al. | |
| 2006/0126794 A1 * | 6/2006 | Hermann | A61B 6/502 378/180 |
| 2006/0239399 A1 | 10/2006 | Lebovic et al. | |
| 2007/0019785 A1 | 1/2007 | Galkin | |
| 2007/0148409 A1 | 6/2007 | Rios et al. | |

FOREIGN PATENT DOCUMENTS

| | | |
|---|---|---|
| FR | 2702059 A1 | 9/1994 |
| WO | WO-96/13211 A1 | 5/1996 |

OTHER PUBLICATIONS

Hanes Industries, Material Safety Data Sheet, Elite Polypropylene Non-Wovens, Hanes Industries, Rev. 2/92, Apr. 8, 2006.
FLEXcon Product Construction Sheet, FLEXmark V-344 Adhesive, Mar. 10, 2006.
Water Ink Technologies, Inc., Technical Datasheet, Versifilm Plus Water Based-Film Inks, Jan. 3, 2005.

* cited by examiner

IMAGING SHEET AND RELATED METHOD

CROSS-REFERENCE TO RELATED APPLICATIONS

This application is a continuation of co-pending U.S. patent application Ser. No. 13/846,114, filed Mar. 3, 2013, now U.S. Pat. No. 8,718,229, which is a continuation U.S. patent application Ser. No. 12/604,049, filed Oct. 22, 2009, now U.S. Pat. No. 8,401,145, which claims the benefit under 35 U.S.C. §119(e) of U.S. Provisional Patent Application No. 61/107,967, filed Oct. 23, 2008, the contents of which are hereby incorporated by reference in their entireties as part of the present disclosure.

FIELD OF THE INVENTION

The present invention generally relates to the fields of radiography and medical imaging, and more particularly, to apparatus and methods for providing comfort to patients during mammography examinations.

BACKGROUND OF THE INVENTION

A mammography examination is a medical procedure for examining a patient's breasts for cancer or other internal conditions. Mammography examinations can be used, for example, to search for tumors or to discern between non-cancerous (benign) and cancerous (malignant) tissues. Mammography examinations are regularly recommended for women over the age of 40, and, when used in concert with self-examinations and physicians' examinations, a mammography examination can be an essential element of a woman's regular care later in life. Early detection through the use of mammography has been shown to reduce mortality rates associated with breast cancer.

During a typical mammography examination, a patient's breasts are positioned within a machine and exposed to a low dose of radiation. The patient's breasts are placed one at a time onto an imaging receptor plate, typically called a "bucky," and pressed substantially flat with the use of a compression device. Radiographic images of the breasts are then recorded and developed as individual photographs, or transferred to a computer for viewing. A doctor, nurse or other medical technician then analyzes the images and assesses the condition of the tissues identified therein.

Although painless, the mammography procedure can be uncomfortable for a patient, for a number of different reasons. A typical bucky contains an X-ray film cassette or digital imaging equipment and is made of metal or hard plastic, which is usually at room temperature when the mammography procedure is commenced. Because room temperature can be thirty to forty degrees cooler than a patient's normal body temperature, the initial contact between the top and front of the bucky and a patient's bare breast or inframammary fold can feel extremely cold. Additionally, the bucky itself defines hard and smooth skin-contacting surfaces that can be uncomfortable to the touch and/or do not promote a feeling of comfort when touched. Further, whether for screening or for diagnosis, a mammography examination can create anxiety in patients, as the procedure requires a patient to disrobe before a technician and to place body parts into a medical device.

A variety of methods and devices has been utilized to ease the discomfort experienced by patients during mammography procedures, but have achieved only limited success. For example, foam padding has been applied to bucky surfaces in an effort to soften them. Although foam can insulate the patient from the temperature of the bucky, foam also can be uncomfortable for the patient, as it tends to stick to a patient's skin and can give the patient a "wetsuit" feeling. This effect can be particularly problematic if the patient perspires during the procedure. Although foam is compressible, foam pads may not reduce the compressive forces associated with placing patients' breasts into mammography devices to levels that are sufficient to outweigh their drawbacks. Further, mammography images are most accurate when the breast is as flat as possible, and therefore if the foam is too thick, it can give rise to distortions in the resulting mammography image.

Yet another drawback of the prior art is that some bucky covers require sterilization of the covers between uses. Other drawbacks of prior art bucky covers is that they can leave adhesive on the bucky surfaces when they are removed which, in turn, requires a technician or other personnel to clean the bucky surfaces of such adhesive residue.

SUMMARY OF THE INVENTION

Accordingly, it is an object of the present invention to overcome one or more of the above-described drawbacks and/or disadvantages of the prior art.

In accordance with a first aspect, the present invention is directed to a covering or sheet to be applied to an imaging receptor plate, or bucky, during a mammography procedure. The cover is preferably substantially incompressible, and may be releasably applied to a bucky before a mammography procedure commences, and removed from the bucky once the mammography procedure is complete. The cover insulates the patient from a difference in temperature between the patient's skin and the bucky, and provides a fresh, sterile surface for each mammography patient.

In currently preferred embodiments of the present invention, the cover comprises a top layer and an adhesive layer affixed to one side of the top layer. Preferably, the top layer is formed of a non-woven polymeric material that imparts a fabric-like or cloth feel. In some embodiments of the present invention, the adhesive layer comprises one or more adhesives that can be acrylic based and can releasably affix the top layer to the surfaces of a bucky. In some such embodiments, the cover is releasably mounted to a liner, and removed from the liner prior to installing the cover onto a bucky.

In some embodiments, the top layer is embossed with a texture, pattern or plurality of raised surface areas and correspondingly recessed surface areas located between the raised surface areas. In some such embodiments, the pattern is a non-directional, repeating pattern, such as a series of rows, of substantially oval or other shaped raised surface areas and correspondingly recessed surface areas. In some such embodiments, the raised surface areas of each row, such as the substantially oval shaped surface areas, are oriented approximately perpendicular to the substantially raised surface areas of adjacent rows.

In some embodiments of the present invention, the top layer is covered with a print pattern. In some such embodiments, the print pattern is floral, or of such nature as to soothe a patient undergoing a mammography examination.

In accordance with another aspect, the present invention is directed to a bucky sheet for releasable attachment to a mammography bucky. The bucky sheet defines a perimeter shape to cover a skin-contacting surface of the bucky and contact a patient's skin during a mammography procedure.

The bucky sheet comprises a sanitary, non-woven polymeric fabric sheet defining a thickness within the range of about 5/1000 inch to about 1/10 inch, a perimeter shape substantially corresponding to the perimeter shape of the bucky, and an exterior surface that contacts the patient's skin during the mammography procedure and is formed of a non-woven fabric having a cloth feel. The non-woven polymeric sheet is substantially incompressible in response to compressive forces exerted thereon during a mammography procedure. The bucky sheet further comprises an adhesive layer underlying the non-woven polymeric fabric sheet that includes an inner surface fixedly secured to the non-woven polymeric fabric sheet, and an exterior surface including thereon a removable adhesive that removably attaches the non-woven polymeric fabric sheet to the skin-contacting surface of the bucky substantially without leaving adhesive residue thereon.

In accordance with another aspect, the present invention is directed to a bucky sheet for releasable attachment to a mammography bucky. The bucky sheet defines a perimeter shape to cover a skin-contacting surface of the bucky and contact a patient's skin during a mammography procedure. The bucky sheet comprises first means formed of a non-woven polymeric material defining a thickness within the range of about 5/1000 inch to about 1/10 inch, a perimeter shape substantially corresponding to the perimeter shape of the bucky, and for contacting the patient's skin during the mammography procedure, thermally insulating the patient's skin from the bucky, imparting a cloth feel to the patient's skin in contact therewith, and for substantially preventing compression of the first means in response to compressive forces exerted thereon during the mammography procedure. The bucky sheet further comprises second means underlying the first means and fixedly secured thereto for removably attaching the first means to the skin-contacting surface of the bucky substantially without leaving residue thereon.

In accordance with another aspect, the present invention is directed to a method for performing a mammography examination. The method comprises the following steps:

(i) providing a mammography apparatus including a bucky;

(ii) adhesively attaching a sanitary, non-woven, polymeric fabric sheet defining a thickness within the range of about 5/1000 to about 1/10 inch, onto a top surface, and if desired, a front surface, of the bucky, and in turn providing the skin-contacting surfaces of the bucky with a sanitary cover formed by the bucky sheet;

(iii) placing a patient's breast onto the bucky sheet, imparting a cloth-like feel from the bucky sheet to the patient's breast, and thermally insulating the patient's breast from the bucky with the bucky sheet;

(iv) compressing the patient's breast between the bucky sheet adhesively attached to the bucky and a compression device;

(v) substantially not compressing the bucky sheet during the compressing step;

(vi) recording a radiographic image of the patient's breast;

(vii) relieving the compression force applied to the patient's breast;

(viii) withdrawing the patient's breast from the bucky; and (ix) removing the bucky sheet from the bucky substantially without leaving any adhesive residue on the bucky.

One advantage of the bucky sheet of the present invention is that it insulates a patient's skin from the relatively cold temperature of a bucky. Another advantage of the bucky sheet of the present invention is that it is incompressible when subjected to the compression forces applied during a mammography procedure. Yet another advantage of the bucky sheet of the present invention is that it has a soft, fabric-like feel. A further advantage of the bucky sheet of the present invention is that it may feature textures, patterns or raised features that contribute to the soft, fabric-like feel, and also may feature a printed design that tends to soothe a patient undergoing a mammography examination. Yet another advantage of the bucky sheet of the present invention is that it provides a sanitary layer atop the bucky for each individual patient.

These and other advantages of the present invention, and/or of the currently preferred embodiments thereof, will become more readily apparent in view of the following detailed description of the currently preferred embodiments and the accompanying drawings.

DETAILED DESCRIPTION OF EMBODIMENTS OF THE INVENTION

Figure 1:
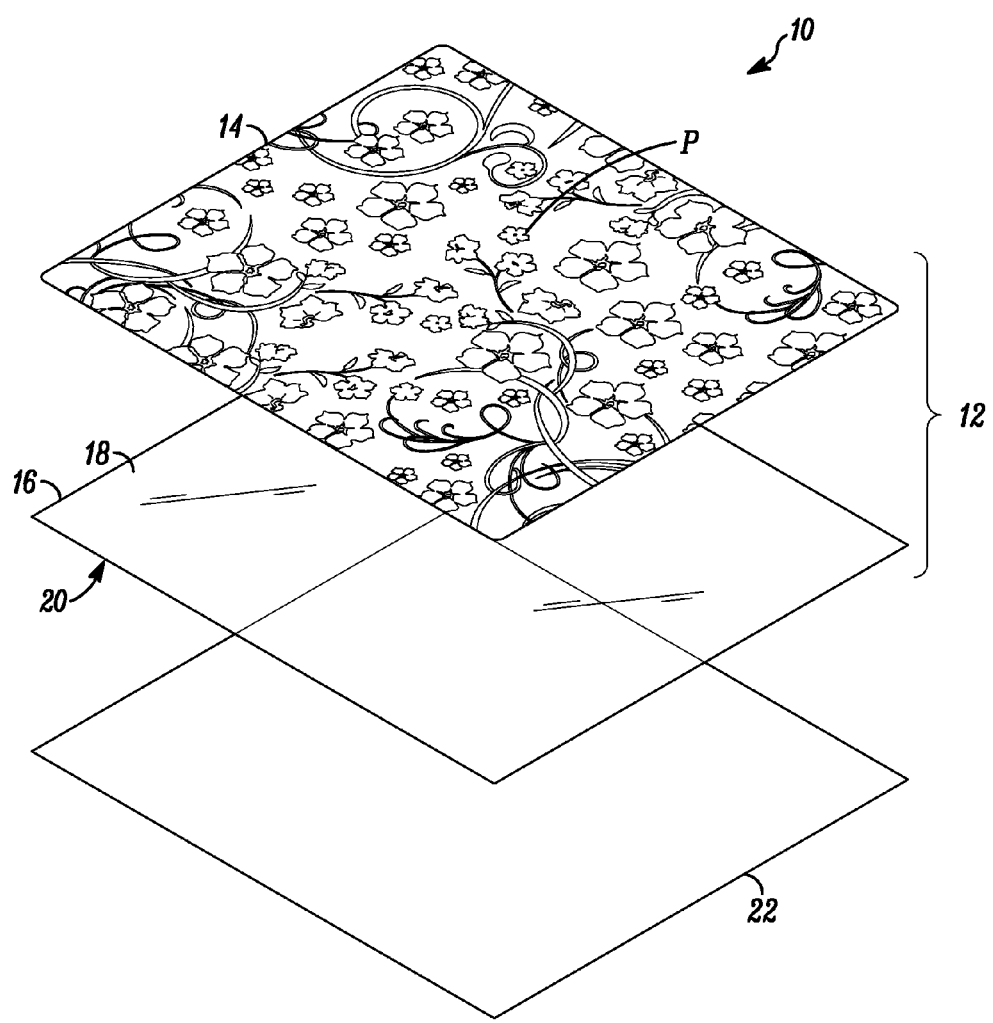
FIG. 1 is an exploded perspective view of an embodiment of a bucky sheet of the present invention.
Figure 2:
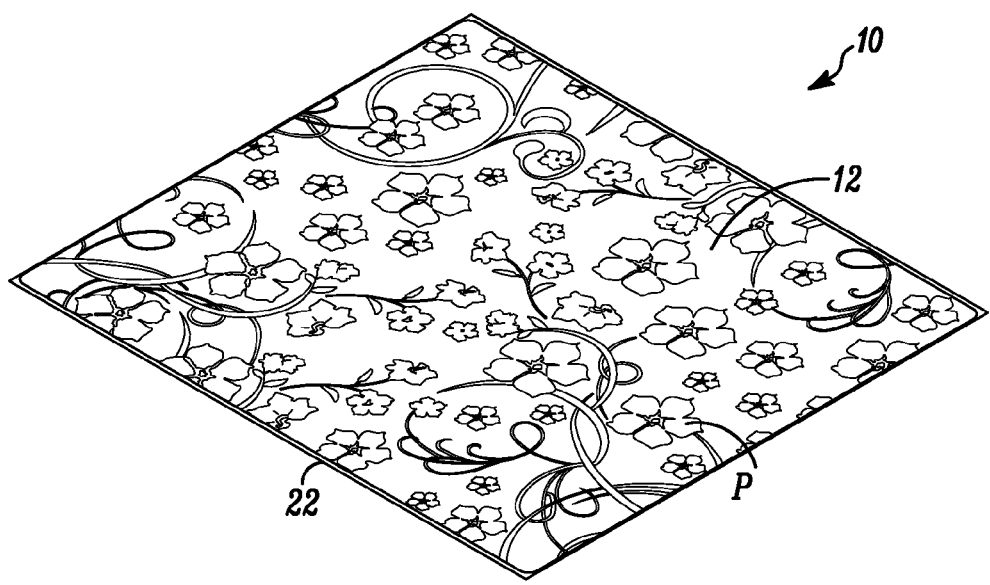
FIG. 2 is an upper perspective view of the bucky sheet of FIG. 1.
Figure 3:
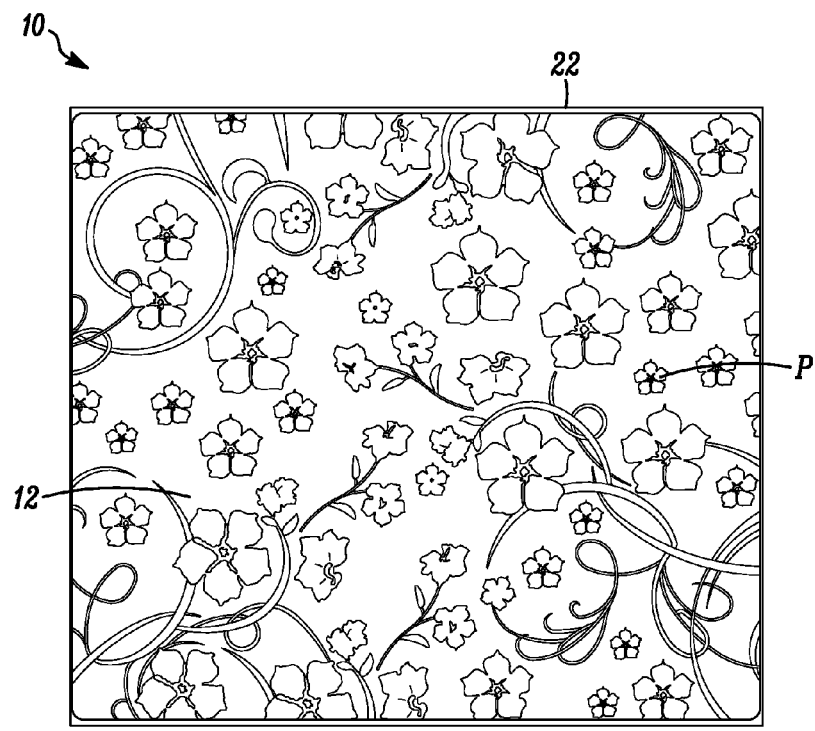
FIG. 3 is a top plan view of the bucky sheet of FIG. 1.

In FIGS. 1 through 4C, a bucky sheet assembly embodying the present invention is indicated generally by the reference numeral 10. As is shown in FIG. 1, the bucky sheet assembly 10 comprises a bucky sheet 12 and a liner 22. The bucky sheet 12 further comprises a top layer 14 and an adhesive layer 16, which are bonded together during the manufacturing process and affixed to the liner 22. In the embodiment shown in FIGS. 1 through 3, a print pattern P is applied to the top layer 14 of the bucky sheet 12. In use, and as described further below, a user removes the bucky sheet 12 from the liner 22, and applies the bucky sheet 12 to the face of a bucky before a mammography examination begins.

The material forming the top layer 14 is selected to remain substantially incompressible in response to the compressive forces applied during a mammography procedure, and to create a durable yet soft external surface that closely resembles woven fabric. The soft fabric-like surface provides a familiar feel to patients who are accustomed to the sensation of clothing or brassieres on their breasts, and also protects against the difference in temperature between the bucky and the patient's breast or inframammary fold. The material forming the top layer 14 is substantially transparent to radiographic imaging so that it substantially does not appear on the mammogram. However, as may be recognized by those of ordinary skill in the pertinent art based on the teachings herein, if desired, portions of the bucky sheet may be partially radiopaque and partially radiolucent (e.g., so that such portions form a shadow on the radiographic image but also allow the viewing of underlying or adjacent tissue detail therethrough), or may be radiopaque (e.g., portions of the sheet may define radiopaque lines forming a grid, or other indicia, such as letters and/or numbers).

Although the top layer 14 may be formed from a variety of different materials and/or composites that are currently known or that later become known, the top layer 14 is preferably formed of a non-woven polymeric fabric, such as polypropylene, which has the feel of a natural cloth or fabric and is comfortable to the touch of a user. In a preferred embodiment, the top layer 14 is formed of spun-bonded polypropylene manufactured by forcing polypropylene resin through a spinneret or similar device to create long, thin strands of non-woven material, which are then gathered together and formed into a random web or mat. Non-woven fibers may be assembled together by mechanically interlocking the fibers, fusing the fibers, or bonding the fibers with a cementing medium. Unlike a woven fabric, non-woven fibers have no real uniformity and are very random in nature. Suitable non-woven fibers which may be used to form the top layer 14 include the Elite® line of non-woven fibers produced by Hanes Companies, Inc., of Conover, N.C. However, any material that is flexible, durable, substantially incompressible and soft to the touch that is currently known, or that later becomes known, may be used to form the top layer 14.

The top layer 14 should be substantially incompressible when subjected to the compression forces in the mammography apparatus. Accordingly, the top layer 14 is thick enough to provide a soft texture to the patient and to insulate the patient from the cold feel of the bucky, but is thin enough to maintain its incompressibility and to be easily packaged. Preferably, the top layer 14 defines a thickness within the range of about $5/1000$ inch to about $1/10$ inch, and more preferably within the range of about $1/100$ inch to about $50/1000$ inch. In the illustrated embodiment, the thickness of the top layer 14 is about is about $10/1000$ inch thick. In addition, the density of the top layer 14 preferably is within the range of about $1/3$ ounce per square yard to about 3 ounces per square yard, and more preferably is within the range of about $1/2$ ounce per square yard to about 2 ounces per square yard. As may be recognized by those of ordinary skill in the pertinent art based on the teachings herein, these materials, dimensions and densities are only exemplary, and numerous other materials, having any of numerous dimensions and/or densities that are currently known, or that later become known, may be employed.

In the illustrated embodiment of the present invention, the top layer 14 is embossed with a texture, pattern and/or a plurality of raised features or surface areas and correspondingly recessed features or surface areas located between raised features or surface areas, that contribute to the soft sensation and/or fabric-like or cloth feel. A preferred pattern is a non-directional series of rows of substantially oval shaped raised surface areas, and correspondingly shaped recessed surface areas located between respective raised surface areas, with the ovals of each row being oriented approximately perpendicular to the ovals of adjacent rows.

As is shown in FIGS. 1 through 4C, in the illustrated embodiment of the present invention, the top layer 14 is covered with a print pattern P. Such print patterns may be floral, as is shown in FIGS. 1 through 4C, or may be defined by any of numerous other patterns or designs that are currently known, or that later become known, and that tends to soothe the patient during the mammography examination experience. Preferably, the print pattern P is printed onto the top layer with a water-based ink and may be covered with a resistant varnish. Suitable inks and varnishes include the Versifilm Plus line of water-based inks and the Water Gloss FDA Overprint Varnish WVG001006, both from Water Ink Technologies, Inc., of Lincolnton, N.C. However, as may be recognized by those of ordinary skill in the pertinent art based on the teachings herein, any of numerous other inks and/or varnishes that are currently known, or that later become known, or materials without ink or varnish, equally may be used.

Also in the illustrated embodiment, the adhesive layer 16 comprises a thin carrier to which an upper adhesive 18 and a lower adhesive 20 have been applied. The upper adhesive 18 is fixedly adhered to the top layer 14, while the lower adhesive 20 releasably adheres to the liner 22 and to a bucky, substantially without leaving any residue behind after the bucky sheet 12 is removed. The adhesives 18, 20 are typically acrylic-based, similar to those utilized in most medical tapes, although neither the upper adhesive 18 nor the lower adhesive 20 is designed or expected to come into contact with a patient's skin. A preferred material for use as an upper adhesive 18 is FLEXcon V344, while a preferred material for use as a lower adhesive 20 is FLEXcon V314, each marketed by FLEXCon Company, Inc., of Spencer, Mass. However, as may be recognized by those of ordinary skill in the pertinent art based on the teachings herein, any of numerous different adhesives that are currently known, or that later become known, equally may be employed. For example, any adhesive that will permanently adhere to the top layer 14 may be utilized as the upper adhesive 18, and any adhesive that will releasably adhere to the liner 22 and to a bucky without leaving a residue upon removal may be used as the lower adhesive 20.

The bucky sheet 12 may be made of any size, so long as the bucky sheet 12 substantially covers, or covers the desired portion or portions of the top and front areas of the bucky that might contact a patient's skin, typically the underside of a breast and the inframammary fold. Typically, the bucky sheet defines a substantially rectangular shape as shown. In such embodiments, the length of the bucky sheet is within the range of about 9 inches to about 17 inches, and the width is preferably within the range of about 7 to about 14 inches. In one currently preferred embodiment, the length is about 13 inches and the width is about 11½ inches. In another currently preferred embodiment, the length is about 11 inches and the width is about 9 inches. Other currently preferred sizes are about 8 inches wide by about 10 inches long, about 10 inches wide by about 12 inches long, and about 14 inches wide by about 17 inches long. The liner 22 is typically substantially coterminous with the bucky sheet 12, but may extend beyond the width or length, or both, of the bucky sheet 12, to enable a user to easily remove the bucky sheet 12 from the liner 22. Additionally, the liner 22 may be sized to permit a plurality of bucky sheets 12 to be rolled or folded for easier storage, delivery or dispensing. As may be recognized by those of ordinary skill in the pertinent art based on the teachings herein, these shapes and dimensions are only exemplary, and the bucky sheets may take any of numerous different shapes and/or dimensions that are currently known, or that later become known.

In the illustrated embodiment, the bucky sheet 12 is assembled by laminating the top layer 14 onto the adhesive 16, which is typically a double-sided adhesive tape layer as described; printing the top layer 14 with any desired image, pattern or text using a suitable ink; and sealing the printed top layer 14 with a suitable varnish.

Figure 4A:
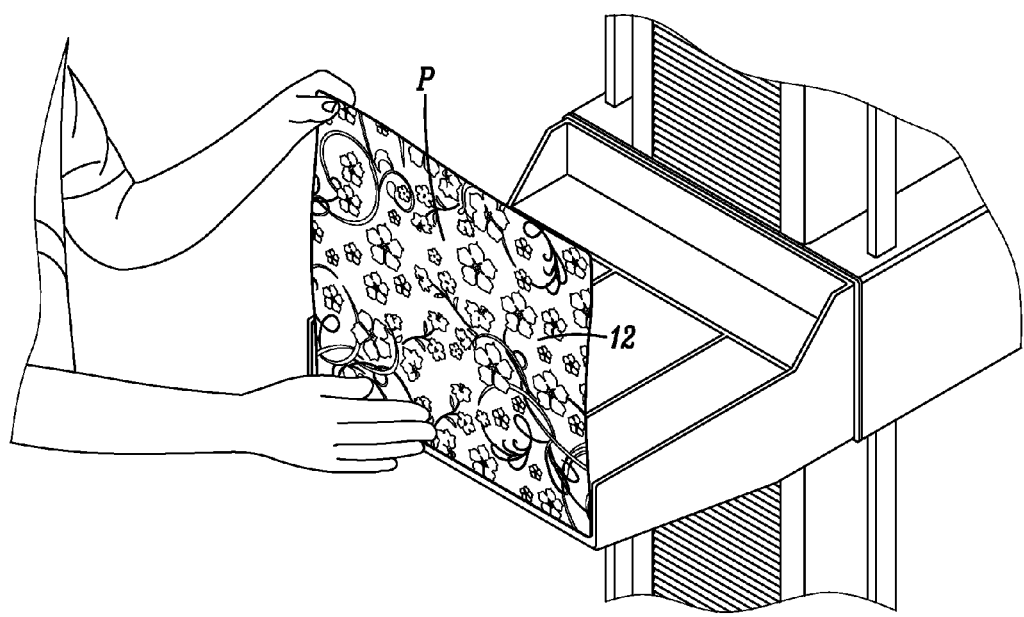
FIGS. 4A, 4B and 4C are perspective illustrations of the application of the bucky sheet of FIG. 1 to a mammography bucky.
Figure 4B:
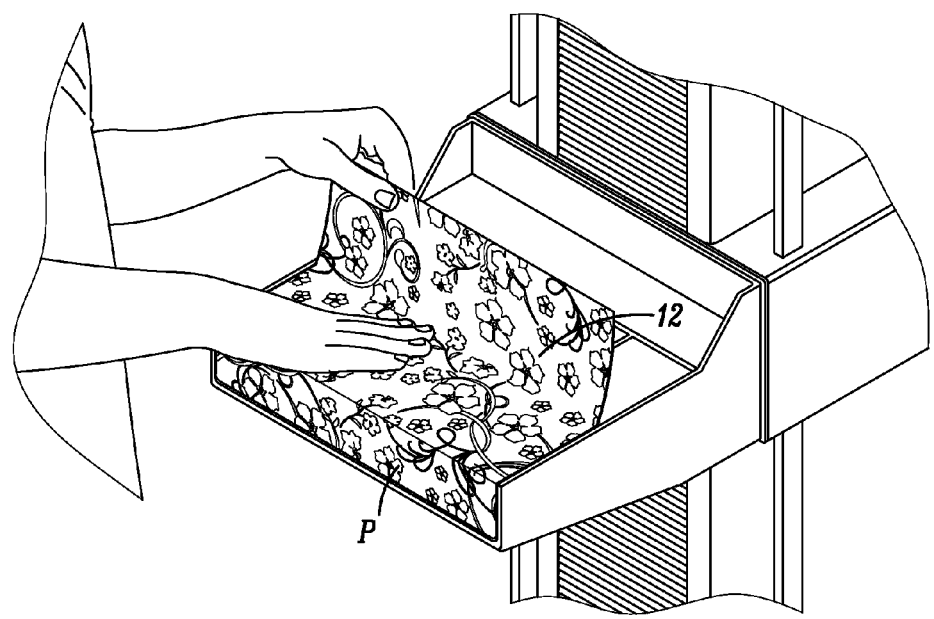
Figure 4C:
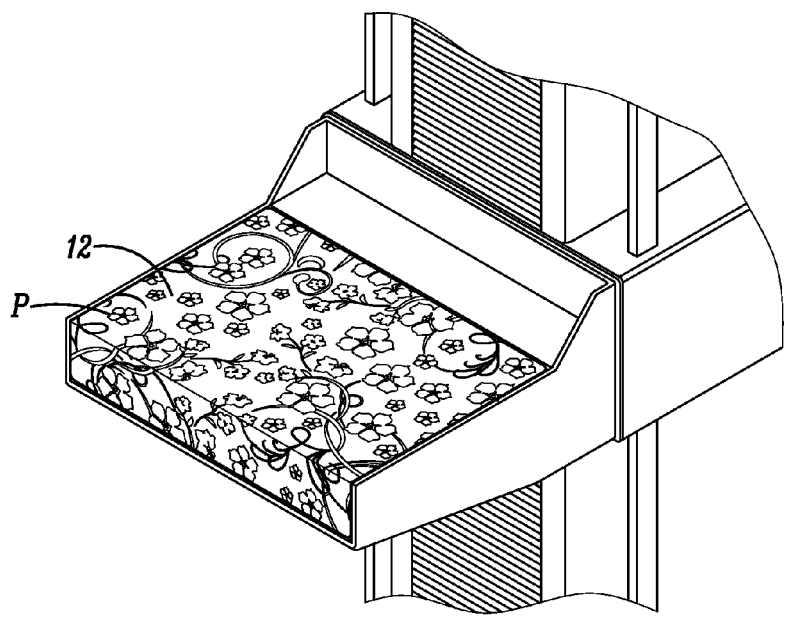

As shown in FIGS. 4A through 4C, in an exemplary use of the bucky sheet 12, a user removes the bucky sheet 12 from the liner 22 and, as is shown in FIG. 4A, places the self-adhesive sheet on the top surface and front edge of the bucky. Next, as is shown in FIG. 4B, a user places a hand onto the bucky and flattens the bucky sheet 12 onto the bucky, ensuring that the bucky sheet 12 covers the top and front surfaces of the bucky which might be placed in contact with the patient's skin. FIG. 4C shows a bucky sheet 12 in place on a bucky. After the mammography procedure is complete, the user can remove the bucky sheet 12 by pulling from a corner or edge, and lifting the bucky sheet 12 from the bucky. Because the bucky sheet 12 does not leave any residue on the bucky, another bucky sheet 12 may be placed onto the bucky without further preparation, and a subsequent mammography procedure may begin momentarily.

In some embodiments of the present invention, a plurality of the bucky sheets are packaged in a box that maintains the bucky sheets in a sanitary condition, and allows the bucky sheets to be readily dispensed therefrom for use. For example, the box containing the plurality of bucky sheets may define a top panel that can be opened to remove a bucky sheet, and closed to retain the remaining bucky sheets therein in a sanitary condition. In other embodiments, the bucky sheet is provided in a respective sterile package, such as a paper or polymeric envelope, that seals the bucky sheet from the ambient atmosphere and maintains the sterility of the bucky sheet until ready for use. In order to use the bucky sheet, the sterile package is torn, or otherwise opened to remove the bucky sheet therefrom, and adhesively attach the bucky sheet to a bucky. One advantage of the bucky sheets of the present invention is that the thin sheet-like configuration of each bucky sheet allows a plurality of such bucky sheets to be packaging one on top of the other, or in a side-by-side relationship, in a relatively small volume box or other packaging enclosure.

Accordingly, an exemplary method of use of the bucky sheet comprises the following steps:

(i) providing a mammography apparatus including a bucky;

(ii) adhesively attaching the sanitary, non-woven, polymeric fabric sheet 12 defining a thickness within the range of about $5/1000$ inch to about $1/10$ inch, onto the skin-contacting surfaces of the bucky, and in turn providing the skin-contacting surfaces of the bucky with a sanitary cover formed by the bucky sheet;

(iii) placing a patient's breast onto the bucky sheet 12, imparting a cloth feel from the bucky sheet to the patient's breast, and thermally insulating the patient's breast from the bucky with the bucky sheet;

(iv) compressing the patient's breast between the bucky sheet 12 adhesively attached to the bucky and a compression device;

(v) substantially not compressing the bucky sheet 12 during the compressing step;

(vi) imaging the patient's breast;

(vii) relieving the compression force applied to the patient's breast;

(viii) withdrawing the patient's breast from the bucky; and (ix) removing the bucky sheet 12 from the bucky substantially without leaving any adhesive residue on the bucky.

It may be readily understood by those having skill in the pertinent art from the present disclosure that any of numerous changes and modifications may be made to the above described and other embodiments of the present invention without departing from the scope of the invention as defined in the appended claims. For example, the bucky sheet may be made of any of numerous different materials, in any of numerous shapes, taking any of numerous different dimensions. In addition, the bucky sheet may be releasably attachable to a bucky in any of numerous different ways that are currently known, or that later become known. For example, rather than use conventional adhesives as described above, the adhesive may be defined by the underlying surface of the bucky sheet being formed of a soft, rubber or rubber-like surface, that forms a relatively high friction or sticky interface with the mammography bucky to prevent relative movement of the bucky sheet and bucky during a mammography procedure. The term "cloth" is used herein to mean a fabric or material formed by weaving, knitting, pressing, or felting natural or synthetic fibers. The phrase "non-woven fabric having a cloth feel" is used herein to means a non-woven fabric that substantially has the texture and/or tactile quality of a woven, knitted or felted material. The term "sheet" is sued herein to mean a broad, relatively thin covering, including without limitation the covering for a mammography bucky. The term "bucky" is used herein to mean a device or surface in a mammography machine for supporting a breast, such as an imaging receptor plate or like imaging receptor surface. Accordingly, this detailed description of the currently preferred embodiments of the present invention is to be taken in an illustrative, as opposed to a limiting sense.

What is claimed is:

1. A sheet for attachment to an imaging surface of a mammography apparatus to cover at least a portion of at least one skin-contacting surface of the imaging surface, the sheet comprising a thin, non-woven polymeric fabric sheet substantially conformable to a shape of the imaging surface and defining an exterior surface for contacting a patient's skin and an opposing interior surface opposing the exterior surface that is releasably attachable to the imaging surface, wherein the non-woven fabric sheet is substantially incompressible in response to compressive forces applied during an imaging procedure.

2. A sheet as defined in claim 1, wherein the exterior surface is embossed with at least one of a texture, a pattern and a raised feature.

3. A sheet as defined in claim 1, wherein the non-woven polymeric fabric sheet defines a thickness within a range of about $5/1000$ inch to about $50/1000$ inch.

4. A sheet as defined in claim 1, wherein the imaging surface is a mammogram bucky.

5. A sheet as defined in claim 1, wherein the imaging procedure is a mammography procedure.

6. A sheet as defined in claim 1, wherein the exterior surface defines a pattern extending throughout substantially the entire exterior surface defined by a repeating pattern of raised surface areas and correspondingly recessed surface areas formed between contiguous raised surface areas.

7. A sheet as defined in claim 1, further comprising a sheet package defining a substantially sterile enclosure receiving therein the sheet and sealing the sheet therein with respect to ambient atmosphere.

8. A sheet as defined in claim 1, wherein the non-woven fabric sheet is incompressible in response to compressive forces applied during an imaging procedure.

9. A sheet as defined in claim 1, wherein the imaging surface comprises an x-ray imaging surface.

10. A mammography method comprising the following steps:

attaching to an imaging surface of a mammography apparatus a sanitary, non-woven, polymeric fabric sheet defining a thickness within a range of about $5/1000$ inch to about $1/10$ inch onto at least a portion of skin-contacting surfaces of the imaging surface, and in turn providing the skin-contacting surfaces of the imaging surface with a sanitary cover formed by the sheet;

capturing breast tissue of a patient between the sheet and a compression device of the mammography apparatus; and imaging the breast tissue.

11. A method as defined in claim 10, wherein the sheet is embossed to facilitate imparting a cloth feel to the patient's breast tissue.

12. A method as defined in claim 10, further comprising packaging the sheet in a sterile enclosure, and storing the sheet in the sterile enclosure until ready for use.

13. A method as defined in claim 10, wherein the imaging surface includes a bucky, and the breast tissue includes at least a portion of the patient's breast.

14. A method as defined in claim 13, further comprising thermally insulating the patient's breast from the imaging surface with the sheet.

15. A method as defined in claim 10, wherein the sheet defines a thickness within a range of about $5/1000$ inch to about $50/1000$ inch.

16. A method as defined in claim 10, further comprising compressing the breast tissue between the sheet and the compression device.

17. A method as defined in claim 16, further comprising substantially not compressing the sheet during the compressing step.

18. A method as defined in claim 10, wherein the imaging surface is defined by a bucky of the mammography apparatus and the bucky includes a top surface and a front surface, the attaching step includes attaching the sheet to the top and front surfaces of the bucky, and the capturing step includes contacting the skin on the underside of the breast with a portion of the sheet attached to the top surface of the bucky, contacting the skin of an inframammary fold of the breast with a portion of the sheet attached to the front surface of the bucky, and capturing the breast between the portion of the sheet attached to the top surface of the bucky and the compression device.

19. A method as defined in claim 18, further comprising thermally insulating the skin of the breast and inframammary fold from the top and front surfaces of the bucky with the sheet.

20. A method as defined in claim 18, wherein the sheet defines (1) a texture, (2) a pattern, and/or (3) a plurality of raised features or surface areas and correspondingly recessed features or surface areas located between raised features or surface areas, and the capturing step includes contacting the skin on the underside of the breast with the texture, pattern or plurality of raised features or surface areas and correspondingly recessed features or surface areas located between raised features or surface areas.

21. A method as defined in claim 10, wherein the imaging surface comprises an x-ray imaging surface.

22. A mammography method comprising:
attaching to an imaging surface of a mammography apparatus a sheet covering at least a portion of at least one skin-contacting surface of the imaging surface, the sheet comprising a non-woven polymeric fabric sheet substantially conforming to a shape of the imaging surface and defining an exterior surface for contacting a patient's skin and an opposing interior surface opposing the exterior surface that is releasably attached to the imaging surface;
capturing breast tissue between the sheet and a compression device of the mammography apparatus; and
imaging the breast tissue.

23. A method as defined in claim 22, wherein the imaging surface includes a bucky, and the breast tissue includes at least a portion of a patient's breast.

24. A method as defined in claim 22, further comprising substantially not compressing the sheet during the imaging step.

25. A method as defined in claim 22, wherein the imaging surface is defined by a bucky of the mammography apparatus and the bucky includes a top surface and a front surface, the attaching step includes attaching the sheet to the top and front surfaces of the bucky, and the capturing step includes contacting the skin on the underside of the breast with a portion of the sheet attached to the top surface of the bucky, contacting the skin of an inframammary fold of the breast with a portion of the sheet attached to the front surface of the bucky, and capturing the breast between the portion of the sheet attached to the top surface of the bucky and the compression device.

26. A method as defined in claim 25, further comprising thermally insulating the skin of the breast and inframammary fold from the top and front surfaces of the bucky with the sheet.

27. A method as defined in claim 25, wherein the sheet defines (1) a texture, (2) a pattern, and/or (3) a plurality of raised features or surface areas and correspondingly recessed features or surface areas located between raised features or surface areas, and the capturing step includes contacting the skin on the underside of the breast with the texture, pattern or plurality of raised features or surface areas and correspondingly recessed features or surface areas located between raised features or surface areas.

28. A method as defined in claim 22, wherein the imaging surface comprises an x-ray imaging surface.

29. A mammography method comprising:
releasably attaching a thin sheet that is substantially incompressible in response to compressive forces applied during an imaging procedure and has a thickness within the range of about $5/1000$ inch to about $1/10$ inch, directly to top and front skin-contacting surfaces of a mammography bucky and substantially conforming the sheet to a shape of the top and front skin-contacting surfaces;
contacting the skin on the underside of a breast with a portion of the sheet attached to the top surface of the bucky, contacting the skin of an inframammary fold of the breast with a portion of the sheet attached to the front surface of the bucky, and capturing the breast between the portion of the sheet attached to the top surface of the bucky and a compression device;
thermally insulating the skin of the breast and inframammary fold from the top and front surfaces of the bucky with the sheet; and
imaging the breast tissue captured between the portion of the sheet attached to the top surface of the bucky and the compression device.

30. A method as defined in claim 29, wherein the mammography bucky comprises an x-ray imaging surface.

* * * * *